United States Patent [19]

Klingler et al.

[11] Patent Number: 5,663,462
[45] Date of Patent: Sep. 2, 1997

[54] PROCESS FOR THE PRODUCTION OF DINITROTOLUENE AND ISOMERIC MIXTURES OF DINITROTOLUENE

[75] Inventors: Uwe Klingler, Dormagen; Thomas Schieb, Rösrath; Gerhard Wiechers, Leverkusen, all of Germany

[73] Assignee: Bayer Aktiengesellschaft, Leverkusen, Germany

[21] Appl. No.: 657,513

[22] Filed: Jun. 4, 1996

[30] Foreign Application Priority Data

Jun. 14, 1995 [DE] Germany ............... 195 21 614.8

[51] Int. Cl.⁶ .................................................. C07C 205/06
[52] U.S. Cl. ................................ 568/934; 568/927; 568/932
[58] Field of Search .......................... 568/934, 932, 568/927

[56] References Cited

U.S. PATENT DOCUMENTS

| | | | |
|---|---|---|---|
| 3,434,802 | 3/1969 | Tolscher et al. | 23/260 |
| 4,021,498 | 5/1977 | Alexanderson et al. | 260/645 |
| 4,496,782 | 1/1985 | Carr | 568/934 |
| 4,650,912 | 3/1987 | Pohl et al. | 568/934 |
| 4,973,770 | 11/1990 | Evans | 568/929 |
| 5,313,009 | 5/1994 | Guenkel et al. | 568/927 |
| 5,345,012 | 9/1994 | Schieb et al. | 568/934 |

FOREIGN PATENT DOCUMENTS

| | | |
|---|---|---|
| 2155562 | 2/1996 | Canada. |
| 436443 | 7/1991 | European Pat. Off.. |

OTHER PUBLICATIONS

T. Urbanski, Chemistry and Technology of Explosives, Pergamon Press (month unavailable) 1964.

*Primary Examiner*—Marianne M. Cintins
*Assistant Examiner*—Dwayne C. Jones
*Attorney, Agent, or Firm*—Joseph C. Gil; Lyndanne M. Whalen

[57] ABSTRACT

Dinitrotoluene and isomer mixtures of dinitrotoluene are produced in a single stage, continuous process by nitrating mononitrotoluene or an isomer mixture of mononitrotoluene in which the ortho-mononitrotoluene content is low with a nitrating acid made up of (1) from about 80 to about 100 wt. % inorganic constituents and (2) up to 20 wt. % organic constituents. The inorganic constituents of the nitrating acid include: (a) from about 60 to about 90 wt. % sulfuric acid, (b) from about 1 to about 20 wt. % nitric acid, and (c) at least 5 wt. % water. The organic constituents of the nitrating acid include: from about 70 to about 100% by weight nitrotoluene isomers and up to about 30% by weight nitration by-products. The nitration reaction is carrier out under adiabatic conditions. The molar ratio of nitric acid to mononitrotoluene during the nitration reaction is generally from about 0.7:1 to about 1.4:1. The phases generated during the nitration are subsequently separated and the acid phase is treated to remove at least 5 wt. % of the water present therein. The water may be removed by distillation or flash vaporization, optionally with simultaneous heat supply. After removal of the water, nitric acid having a concentration of from about 50 to about 100 wt. % is added to the treated acid phase in amount sufficient to satisfy the compositional limits for a nitrating acid useful in the process of the present invention. This reconcentrated acid phase is then returned to the nitration reaction.

8 Claims, No Drawings

PROCESS FOR THE PRODUCTION OF DINITROTOLUENE AND ISOMERIC MIXTURES OF DINITROTOLUENE

BACKGROUND OF THE INVENTION

The present invention relates to a continuous process for the production of dinitrotoluene and isomeric mixtures thereof by single-stage nitration of mononitrotoluene under adiabatic conditions.

Dinitrotoluene (DNT) is an intermediate for the production of tolylene diisocyanate (TDI). DNT is obtained industrially by reacting toluene with nitrating acid which is a mixture of nitric and sulfuric acids (See, e.g., DE-B 1 468 362; T. Urbanski, *Chemistry and Technology of Explosives*, Pergamon Press 1964; and Ullmann's *Encyclopädie der technischen Chemie*, 4th Edition, vol. 17, p. 392, Verlag Chemie, Weinheim 1979).

This known nitration process is carried out isothermally, that is, the heat of reaction is dissipated at its place of origin by a coolant. Large amounts of energy are used and the resultant process is complicated and expensive.

Adiabatic nitration processes have been more and more successful recently. See, e.g., EP 0,373,966; EP 0,436,443; U.S. Pat. No. 5,313,009; and EP 0,597,361. In the processes described in these disclosures, the heat of reaction is not dissipated by cooling. That heat is left in the system and used to concentrate the waste acid.

A further advantage of these adiabatic processes is that dilute nitric acids which are considerably cheaper than the highly concentrated acid can be used. While dilute grades of nitric acid can in principle also be used in the known isothermal processes, the additional energy expenditure is considerable.

EP 0,373,966, EP 0,436,443 and U.S. Pat. No. 5,313,009 each describes adiabatic nitration of aromatic compounds with a nitrating acid which is a mixture of sulfuric and nitric acids to produce mononitrated compounds from hydrocarbons. However, nitration of a compound which already has nitro groups to produce a multiply nitrated compound is not described. The examples exclusively describe the nitration of benzene. No example mentions toluene as an aromatic compound to be nitrated.

EP 0,597,361 describes the manufacture of DNT by an adiabatic process. In this process, DNT is obtained in one stage by reaction of toluene with nitrating acid. The mononitration of mononitrotoluene to form DNT is not disclosed.

A disadvantage of the process described in EP 0, 597,361 is the greater proportion of ortho-DNT obtained in comparison to isothermal processes. This is attributable to the higher reaction temperature during the nitration, especially during the mononitration. Ortho-DNT is an unwanted mixture of DNT isomers having nitro groups in the ortho position (i.e., the 2,3- and 3,4-DNT isomers), which cannot be used in TDI manufacture. It is therefore a waste product and must be separated and disposed of at considerable expense.

Even the conventional, isothermal nitration process produces a certain proportion of ortho-DNT, although this proportion is not as high as that produced in the adiabatic processes. The removal of the ortho-DNT isomers is usually carried out after hydrogenation to produce the corresponding amine. This removal requires a column giving very good separation because the boiling point of the product to be separated off (i.e., the amines produced from the ortho-DNT) is only slightly different from that of the desired amine. It is therefore necessary to set a high reflux ratio which drives the distillation costs sharply upwards. Because no use exists for the separated ortho amine, increased production of this amine product is equivalent to a loss of yield. Moreover, an increased production of ortho-DNT increases the cost of the hydrogenation process and necessitates the destruction of the unwanted product.

Another disadvantage of the known adiabatic nitration process becomes evident during the concentration of the waste acid. This waste acid contains dissolved organics, essentially dissolved DNT. The latter is steam-volatile and is largely steamed out concurrently during the concentration of the waste acid. The modern and reliable vacuum processes require low-condensation conditions for the vaporized water. At the temperatures used to concentrate the waste acid, DNT crystallizes out and forms deposits in the condensation system.

This problem also exists in the known isothermal processes. However, in the isothermal processes, mononitrotoluene (MNT) may be injected into the hot vapors (DE-A 3,409,719) so that the condensate from the vapors is kept liquid by melting point depression and blockages are avoided. This is not possible in the case of the known adiabatic process, since no isolated MNT is present in the process.

SUMMARY OF THE INVENTION

It is an object of the present invention to provide an adiabatic process for the production of dinitrotoluene in which the ortho-DNT content is lower than that achieved by known processes.

It is also an object of the present invention to provide a process for the production of dinitrotoluene in which spent nitrating acid can be reconcentrated and reused without the formation of unwanted deposits.

These and other objects which will be apparent to those skilled in the art are accomplished by nitrating mononitrotoluene satisfying specific compositional requirements with a nitrating acid satisfying specific compositional requirements under adiabatic conditions and in amounts such that the molar ratio of nitric acid to mononitrotoluene is from about 0.7:1 to about 1.4:1. The phases which form during this reaction are separated. The desired DNT product is recovered from one phase. The second, acid phase, is treated to remove at least 5% by weight water and nitric acid is then added to that treated acid phase in an amount sufficient to make the nitric acid content of that phase come within the range of amounts required for the nitrating acid to be used to nitrate more MNT. The nitric acid added generally has a concentration of from about 50 to about 100%. This reconcentrated acid phase is then recycled and reused to nitrate additional MNT.

DETAILED DESCRIPTION OF THE INVENTION

The present invention relates to a single-stage process for the continuous production of dinitrotoluene and isomer mixtures thereof having a low ortho-DNT content. In this process, MNT having an m-isomer content less than or equal to 4.5 wt. %, preferably from about 3.5 to 4.5 wt. %, is nitrated with nitrating acid under adiabatic conditions and in amounts such that the molar ratio of nitric acid to MNT is from about 0.7:1 to about 1.4:1, preferably from about 0.8:1 to about 1.2:1. The nitrating acid used is made up of: (1) from about 80 to 100 wt. %, preferably from about 90 to 100 wt. %, of inorganic constituents and (2) up to about 20 wt.

%., preferably up to 10 wt. %, organic constituents. The inorganic constituents in (1) include: (a) from about 60 to about 90 wt. %, preferably from about 65 to about 85 wt. %, sulfuric acid; (b) from about 1 to about 20 wt. %, preferably from about 1 to about 10 wt. %, nitric acid; and (c) at least 5 wt. %, preferably from about 10 to about 30 wt. %, water. The organic constituents in (2) include: (a) from about 70 to 100 wt. %, preferably from about 90 to 100 wt. %, nitrotoluene isomers and (b) up to 30 wt. %, preferably up to 10 wt. %, nitration by-products. The phases which form during nitration are subsequently separated. The acid phase is treated to remove at least 5 wt. %, preferably from 5 to 30 wt. %, of the water. This removal may be accomplished by distillation or by flash vaporization, optionally with simultaneous heat supply. After water has been removed, nitric acid is added to the acid phase in an amount sufficient to satisfy the compositional requirements of the nitrating acid to be used to nitrate MNT in accordance with the present invention. The nitric acid added generally has a concentration of from about 50 to about 100% by weight, preferably from about 60 to about 80% by weight. The thus-treated acid phase is then returned to the nitration stage.

MNT is preferably added to the vapors generated during the concentration of the acid phase before those vapors are condensed. The amount of MNT added is chosen so that the vapor condensate is discharged as liquid and forms no solid deposits. No solid deposits are generally obtained if the weight ratio of MNT to DNT is 2:1 to 10:1, preferably 2:1 to 5:1 in the vapor condensate. After the phase separation, the organic constituents of the vapor condensate are returned to the nitration stage.

The process of the present invention is preferably carried out at temperatures of 60° to 200° C. and pressures of 1 to 100 bar.

The ortho-DNT content of DNT produced by the process of the present invention does not exceed the ortho-DNT contents of DNT produced by the conventional isothermal process. Through the adiabatic mode of operation, the heat of reaction is used in the process and dilute nitric acid can be used. In the process of the present invention, the o-DNT content is generally about 4.0 wt. %, relative to DNT.

The process of the present invention is particularly advantageous when MNT (preferably manufactured by isothermal means) having a small proportion of m-isomer is used.

The invention is further illustrated but is not intended to be limited by the following examples in which all parts and percentages are by weight, unless otherwise specified.

EXAMPLES

Example 1

137 g/h (1 mol/h) mononitrotoluene isomer mixture (isomer distribution: ortho/meta/para=59.9/4.3/38.8 wt. %) and 1890 g/h (1.08 mol/h) nitrating acid composed of 77.9% by weight $H_2SO_4$, 3.6% by weight $HNO_3$ and 38.8% by weight $H_2O$ were reacted continuously at a starting temperature of about 120° C. under adiabatic conditions. After separation of the phases, the acid phase was concentrated in vacuum. To avoid deposits in the condensation section, 9 g/h MNT were added to the superheated vapors of the evaporator. The concentrated waste acid, after being strengthened with 60% nitric acid, was returned to the adiabatic nitration stage as were the organic constituents of the vapor condensate. 180 g/h (99 wt. %) dinitrotoluene isomer mixture were isolated. Its o-DNT content was 4.1 wt. %.

Example 2

137 g/h (1 mol/h) mononitrotoluene isomer mixture (isomer distribution: ortho/meta/para=59.9/4.3/38.8 wt. %) and 587 g/h (1.08 mol/h) nitrating acid composed of 73.6% weight $H_2SO_4$, 11.6% by weight $HNO_3$ and 14.8% by weight $H_2O$ were reacted continuously at a starting temperature of about 60° C. under adiabatic conditions. After separation of the phases, the acid phase was concentrated in vacuum. To avoid deposits in the condensation section, 4.5 g/h MNT were added to the superheated vapors of the evaporator. The concentrated waste acid, after being strengthened with 98.5% nitric acid, was returned to the adiabatic nitration stage, as were the organic constituents of the vapor condensate. 180 g/h (99 wt. %) dinitrotoluene isomer mixture were isolated. Its o-DNT content was 4.1 wt. %.

Example 3

137 g/h (1 mol/h) mononitrotoluene isomer mixture (isomer distribution: ortho/meta/para=59.9/4.3/38.8 wt. %) and 1173 g/h (1.08 mol/h) of a nitrating acid composed of 76.9% by weight $H_2SO_4$, 5.8% by weight $HNO_3$ and 17.3% by weight $H_2O$ were reacted continuously at a starting temperature of about 100° C. under adiabatic conditions. After separation of the phases, the acid phase was concentrated in vacuum. To avoid deposits in the condensation section, 7 g/h MNT were added to the superheated vapors of the evaporator. The concentrated waste acid, after being strengthened with 68% nitric acid, was returned to the adiabatic nitration stage, as were the organic constituents of the vapor condensate. 180 g (99 wt. %) dinitrotoluene isomer mixture were isolated. Its o-DNT content was 4.0 wt. %.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the production of dinitrotoluene or an isomeric mixture of dinitrotoluene comprising:

a) nitrating mononitrotoluene or an isomeric mixture of mononitrotoluene having a meta-MNT content less than or equal to 4.5% by weight with a nitrating acid made up of:
   (1) from about 80 to about 100% by weight of inorganic constituents which include:
      (a) from about 60 to about 90% by weight sulfuric acid,
      (b) from about 1 to about 20% by weight nitric acid, and
      (c) at least 5% by weight water and
   (2) up to 20% by weight organic constituents which include:
      (a) from about 70 to about 100% by weight isomers of nitrotoluene and
      (b) up to 30% by weight nitration by-products under adiabatic conditions and in amounts such that the molar ratio of nitric acid to mononitrotoluene is from about 0.7:1 to about 1.4:1, b) separating acid and dinitrotoluene-containing phases formed during a), c) removing at least 5% by weight water from the acid phase separated in b), d) adding nitric acid having a concentration of from about 50 to about 100% to the acid phase from c) in an amount sufficient to bring the nitric acid content within the requirements of a), e) returning the acid phase from d) to the nitrating acid used in step a), and f) recovering the dinitrotoluene isomer mixture from the dinitrotoluene-containing phase separated in b).

2. The process of claim 1 in which the water is removed in step c) by distillation.

3. The process of claim 1 in which the water is removed in step c) by flash vaporization.

4. The process of claim 1 in which an isomeric mixture of mononitrotoluene having a meta-mononitrotoluene content of from about 3.5 to about 4.5% by weight is nitrated.

5. The process of claim 1 in which the nitrating acid is composed of about 90% by weight inorganic constituents and about 10% by weight organic constituents.

6. The process of claim 1 in which the inorganic constituents of the nitrating acid include: (a) 65–85% by weight sulfuric acid, (b) 1–10% by weight nitric acid, and (c) up to 10% by weight water.

7. The process of claim 1 in which the molar ratio of nitric acid to mononitrotoluene is from about 0.8:1 to about 1.2:1 in step a).

8. The process of claim 1 in which mononitrotoluene is added during c).

* * * * *